United States Patent [19]

Hinnenkamp et al.

[11] 4,188,490
[45] Feb. 12, 1980

[54] CATALYTIC OXIDATION OF ETHYLENE TO MIXTURES OF ACETIC ACID AND VINYL ACETATE

[75] Inventors: James A. Hinnenkamp, Cincinnati, Ohio; John A. Scheben, Erlanger, Ky.

[73] Assignee: National Distillers and Chemical Corporation, New York, N.Y.

[21] Appl. No.: 801,282

[22] Filed: May 27, 1977

[51] Int. Cl.² ...................... C07C 53/08; C07C 67/00
[52] U.S. Cl. ..................................... 560/245; 562/548
[58] Field of Search ................... 260/533 R; 560/245; 562/548

[56] References Cited
FOREIGN PATENT DOCUMENTS
2529365 1/1976 Fed. Rep. of Germany .

Primary Examiner—Bernard Helfin
Assistant Examiner—Michael Shippen
Attorney, Agent, or Firm—Kenneth D. Tremain

[57] ABSTRACT

Ethylene and oxygen are reacted in the presence of steam in the vapor phase within the temperature range of from about 150° C. to about 250° C. in contact with a catalytically effective amount of palladium metal on a zinc oxide support in the presence of a sulfur modifier to provide mixtures of acetic acid and vinyl acetate.

9 Claims, No Drawings

CATALYTIC OXIDATION OF ETHYLENE TO MIXTURES OF ACETIC ACID AND VINYL ACETATE

BACKGROUND OF THE INVENTION

1. Field of the Invention

This invention relates to the field of processes for the catalytic oxidation of ethylene to acetic acid and vinyl acetate, and more particularly, to such processes yielding mixtures of these products.

2. Description of the Prior Art

Numerous processes are known for the catalytic oxidation of ethylene to acetic acid, often in admixture with some acetaldehyde. See, for example U.S. Pat. Nos. 3,792,087 and 3,970,697.

Similarly, numerous processes are known for the catalytic conversion of ethylene and acetic acid to vinyl acetate. Such processes are described in U.S. Pat. Nos. 3,190,912; 3,637,819, and 3,650,896.

According to U.S. Pat. No. 3,637,818, mixtures of acetaldehyde, acetic acid and vinyl acetate can be prepared directly from ethylene by reacting this olefin with oxygen and water in the liquid phase in the absence of mineral acids and anions other than acetate ions, and in the presence of a noble metal such as palladium, and a manganese and/or cobalt acetate.

SUMMARY OF THE INVENTION

It has very surprisingly been found that ethylene can be converted in a single-step catalytic oxidation process to mixtures of acetic acid and vinyl acetate, both products being of substantial commercial importance.

Briefly stated, the process of this invention comprises reacting ethylene and oxygen in the presence of steam within the temperature range of from about 150° C. to about 250° C. in the vapor phase in contact with a catalytically effective amount of a catalyst system comprising palladium metal on a zinc oxide support in the presence of a sulfur-containing catalyst modifier.

The acetic acid can be recovered as such from the vinyl acetate employing known and conventional techniques, for example, fractional distillation; alternatively, the acetic acid contained in the product mixture can be converted in situ to an alkali metal salt such as sodium acetate, also a commercially valuable product, by the addition of an aqueous solution of the corresponding alkali metal salt of an acid weaker than acetic acid. The product mixture will form an aqueous phase containing the acetic acid salt and a water-insoluble vinyl acetate phase.

DESCRIPTION OF THE PREFERRED EMBODIMENTS

In accordance with this invention, a reactant feed comprising ethylene, oxygen and water (as steam) is contacted in the vapor phase with a catalyst composition as hereinafter more fully described to provide mixtures of acetic acid and vinyl acetate. The gaseous mixture can be contacted with the catalyst in any suitable manner, whether by maintaining the latter in a fixed or moving bed or by utilizing fluidized bed operations.

The reaction is carried out at temperatures within the range of from about 150° C. to about 250° C., and advantageously, at up to about 220° C. Temperatures greater than the latter value may result in undue ethylene combustion and increase side reactions, e.g., ethylene copolymerization. Either atmospheric or elevated pressures can be used, the use of higher pressures tending to increase product conversions. The reaction can thus be effected at pressures of up to about 20 atmospheres. It is, however, generally preferred to carry out the vapor phase process under pressures only slightly in excess of atmospheric, e.g., from about 3 to about 10 atmospheres to increase productivity and catalyst efficiency.

The ethylene may be employed in the pure form or can be impure in the sense that it may contain as an inert diluent, minor amounts, e.g., up to about 50 mol percent hereof, incorporated in the feed mixture, of a saturated hydrocarbon such as methane, ethane or propane. The oxygen in the feed can similarly be pure oxygen or an oxygen containing gas mixture such as air or air enriched with oxygen. In addition to these materials, the feed mixture reacted in the process of this invention can contain other inert diluents such as carbon dioxide or nitrogen. The relative amount of water (as steam) can range from about 0.2 to about 10, preferably about 1 to about 8, moles per mole of oxygen.

The catalyst support herein comprises zinc oxide. In a preferred mode, the zinc oxide comprises from about 5 to about 95 weight percent of the support, the balance of the support being selected from among any of the known and conventional catalyst support materials such as silica, alumina, silica-alumina, carbon such as activated carbon or the like, titania, zirconia, glass beads, diatomaceous earth, and similar substances. The support as impregnated or loaded with the sulfur modifier and the palladium metal, whether alone or admixed, alloyed, or in solid solution with a further metal, e.g., a material selected from Groups IB or VIII of the Periodic Table of the Elements appearing on pages 60–61 of Lange's Handbook of Chemistry (Revised 10th Edition), is deposited on the support. The catalytically effective palladium metal and sulfur modifier can be deposited on or impregnated in the catalyst carrier in any desired manner or sequence, the combined supported catalyst composition however formed being active in the process of this invention.

The palladium metal is incorporated in amounts of from about 0.01% to about 6%, preferably from about 0.1% to about 5%, by weight of the supported catalyst composition. A combined palladium-gold catalyst is useful since the gold improves the catalyst stability and promotes activity. The gold content can be about 0.01% to about 5%, preferably about 0.1% to about 3%, by weight of the supported catalyst composition. The weight ratio of palladium to gold can vary between about 1:3–3:1 and is preferably about 2:1.

Deposition of the catalytic metals on the support is effected by conventional techniques.

We have found that certain sulfur containing modifiers show utility in modifying the noble metal catalyst in a manner to promote the oxidation of ethylene in the vapor phase to mixtures of acetic acid and vinyl acetate. The modifiers found applicable include sulfur dioxide, sulfur trioxide, sulfuric acid, sulfurous acid, trifluoromethanesulfonic acid, p-toluenesulfonic acid, potassium acid sulfate, magnesium sulfate, and aluminum potassium sulfate.

Further sulfur modifiers useful in the present invention include:

(a) compounds of the formula, R-Z in which R is alkyl, aryl, aralkyl or alkaryl of up to about 8 carbon atoms and Z is —SH, —SR', —SSR', R'SO—, R'SO$_2$— or

wherein R" is H or lower alkyl and R' has the same meaning as R;

(b) cyclic compounds containing a hetero sulfur atom; and (c) thiourea and N-lower alkyl thiourea.

Sulfur-containing modifiers (a), (b) and (c) above which can be employed in accordance with this invention thus include;

thiols, such as alkyl, aryl, alkaryl and aralkyl thiols exemplified by propanethiol, pentanethiol, tolylthiol, phenylthiol, benzylthiol and phenethylthiol, as well as the corresponding sulfides, disulfides, sulfones and sulfoxides, exemplified by diphenyl sulfide, diethyl disulfide, dimethyl sulfoxide, dipropyl sulfone, dibenzyl sulfide, diphenyl disulfide, diethyl sulfide, and the like;

thioamides, such as thioalkanoamides exemplified by thioacetamide, N-methyl thioacetamide, thiocaproamide and N,N-dimethyl thiopropionamide;

Sulfur-heterocyclic compounds including thiophene, phenothiazine, thiazole, benzothiophene, and the like, and corresponding sulfones and sulfoxides thereof; and thiourea and N-methyl thiourea.

The preferred sulfur modifiers used in this invention have at least two atoms of oxygen, and can have three to four atoms of oxygen, associated with each sulfur atom. The preferred modifiers are thus either oxides or inorganic and organic acids and the salts thereof. The oxides are SO$_2$ and SO$_3$, and the inorganic acids are sulfurous acid and sulfuric acid. The organic acids are sulfonic acids, containing a sulfur attached to a carbon atom, e.g., β-naphthalene sulfonic acid, dodecanesulfonic acid and 1,3,6-naphthalene sulfonic acid. Applicable salts of inorganic and organic acids include Group I through Group IV metal and transition metal salts such as sodium benzene sulfonate, cobalt sulfate and potassium sulfite.

Mixtures of the aforesaid modifiers can also be employed.

The concentration of the sulfur-containing modifier herein can range from about 0.05% to about 25%, preferably about 0.1% to about 15%, by weight of the supported catalyst composition.

The palladium metal zinc oxide supported catalyst is preferably treated with sulfur dioxide in the temperature range of from about 25° C. to about 300° C. Gaseous sulfur dioxide can be fed over the catalyst at the desired temperature either in the pure state or diluted with air or nitrogen. An active catalyst can also be prepared by passing moist air and sulfur dioxide gas over the catalyst within the foregoing temperature range. Aqueous solutions of SO$_2$ can be prepared by saturating water at various temperatures with gaseous SO$_2$ and the resulting sulfurous acid solutions can be used to impregnate the catalyst.

Sulfur trioxide is a liquid at room temperature. It is convenient to modify the catalyst with SO$_3$ by passing its vapors over the catalyst at 25°–200° C. An inert gas such as nitrogen, argon or helium, serves to carry the SO$_3$ vapors over the catalyst.

Sulfuric acid, trifluoromethanesulfonic acid, p-toluenesulfonic acid, potassium acid sulfate, cobalt sulfate, manganese sulfate, and aluminum potassium sulfate, are added to the catalyst by impregnating with aqueous solutions of the desired sulfur modifier. The catalyst is then dried before use.

It will be recognized by those skilled in the art that additional quantities of the sulfur modifiers can be added to the reaction zone continuously or intermittently during the course of the reaction. As just one example, the sulfurous acid solutions can be incorporated into water being fed to the reaction zone.

Example 1 illustrates the criticality of the temperature range herein. Examples 2 to 7 are illustrative of the invention. Throughout this specification and claims, all parts and percentages are by weight and all temperatures are in degrees centigrade unless otherwise specified. Further, as employed herein, the "selectivity" of a product's formation is defined as follows:

$$\% \text{ Selectivity} = \frac{\text{Moles of product formed}}{\text{Moles of specified reactant reacted}} \times 100$$

EXAMPLE 1

A zinc oxide-alumina oxide catalyst support containing 24% by weight of zinc oxide is impregnated in a routine manner with 0.5% by weight of palladium metal and placed in a reactor. A constant flow of moist air containing SO$_2$ was passed over the catalyst at 200° C. for one hour and the reactor was thereafter cooled. Ethylene, oxygen and water were introduced into the reactor in a molar ratio of 5:1:4 and a pressure of nearly 7 atmospheres. The reactor contents were heated to 130° C. Hourly analysis of the reaction products and vent gases showed an oxygen conversion of only 2%, an ethylene selectivity for acetic acid of 89%, for vinyl acetate of 0%, and for carbon dioxide of 11%. Space time velocity was 262. Catalyst efficiency calculated for acetic acid was 0.8 g per g of palladium metal/hr. No acetaldehyde was detected.

EXAMPLE 2

Example 1 was repeated, however, the reaction was conducted at 150° C. and 5 atmospheres. Hourly, there was 34% oxygen conversion, a selectivity of ethylene for acetic acid of 33%, for vinyl acetate of 22%, and for carbon dioxide of 45%. Space time velocity was 271. Catalyst efficiency calculated for acetic acid was 3.0 g per g of palladium metal/hr. and for vinyl acetate, 2.8. No acetaldehyde was detected.

EXAMPLES 3 to 7

Examples 3 to 7 were carried out in a manner identical to that of Example 2, the following changes in procedure being noted:

TABLE

| EXAMPLE | Hours on Stream | Reaction Temp. | Pressure (atmos.) | % O$_2$ Conv. | % C$_2$H$_4$ Selectivity | | | Hourly g VA/g Pd | Hourly g HO Ac g Pd |
| | | | | | HOAc | Vinyl Acetate | CO$_2$ | | |
|---|---|---|---|---|---|---|---|---|---|
| 3 | 19 | 150 | 5 | 32 | 38 | 18 | 44 | 2.2 | 3.3 |
| 4 | 43 | 150 | 5 | 33 | 35 | 18 | 38 | 3.6 | 3.4 |

TABLE-continued

| EXAMPLE | Hours on Stream | Reaction Temp. | Pressure (atmos.) | % O$_2$ Conv. | % C$_2$H$_4$ Selectivity | | | Hourly g VA/g Pd | Hourly g HO Ac g Pd |
| --- | --- | --- | --- | --- | --- | --- | --- | --- | --- |
| | | | | | HOAc | Vinyl Acetate | CO$_2$ | | |
| 5 | 46 | 150 | ~7 | 22 | 38 | 21 | 41 | 2.5 | 3.2 |
| 6 | 63 | 150 | ~7 | 23 | 42 | 16 | 42 | 1.9 | 3.6 |
| 7 | 85 | 150 | ~7 | 32 | 38 | 13 | 49 | 1.9 | 4.2 |

No acetaldehyde beyond trace amounts was detected in any of the above examples.
Space time velocities for these examples ranged from 271 to 275.
VA = Vinyl Acetate
HOAc = Acetic Acid
Pd = Palladium

What is claimed is:

1. A process for catalytically oxidizing ethylene to mixtures of acetic acid and vinyl acetate which comprises reacting ethylene and oxygen in the presence of steam within the temperature range of from about 150° C. to about 250° C. in the vapor phase in contact with a catalytically effective amount of a catalyst system comprising palladium metal on a zinc oxide support in the presence of a sulfur-containing catalyst modifier having from two to four atoms of oxygen associated with each sulfur atom.

2. The process of claim 1 wherein the reaction is carried out at a pressure of from about 3 to about 10 atmospheres.

3. The process of claim 1 wherein the zinc oxide is present in an amount of from about 5 to about 95 weight percent of the entire support.

4. The process of claim 1 wherein the sulfur-containing modifier is selected from the group consisting of sulfur dioxide, sulfur trioxide, sulfurous acid, a sulfonic acid, and a salt of said acids.

5. The process of claim 4 wherein the sulfur-containing modifier is selected from the group consisting of sodium benzene sulfate, cobalt sulfate, potassium sulfate, trifluoromethanesulfonic acid, p-toluenesulfonic acid, potassium acid sulfate, manganese sulfate, and aluminum potassium sulfate.

6. The process of claim 5 wherein the sulfur-containing modifier is present in an amount of about 0.05% to about 25% by weight of the supported catalyst.

7. The process of claim 1 wherein said catalytically effective amount of palladium metal is about 0.01% to about 6% by weight of the supported catalyst.

8. The process of claim 1 wherein the mixture of ethylene, oxygen and water contains from about 5 to about 20 mole percent of oxygen and from about 0.2 to about 10.0 moles of water vapor per mole of oxygen.

9. A process for catalytically oxidizing ethylene to mixtures of acetic acid and vinyl acetate which comprises reacting ethylene with oxygen in the presence of steam within the temperature range of from about 150° C. to about 250° C. in the vapor phase in contact with a supported catalyst system containing from about 0.01% to about 6% palladium metal by weight of the support, said support comprising zinc oxide, the zinc oxide being present therein at from about 5.0 to about 95.0 weight percent of the support, it being further provided that the supported catalyst is impregnated with from about 0.05% to about 25% by weight thereof with a member of the group consisting of sulfur dioxide, sulfur trioxide, sulfurous acid, sulfuric acid, a sulfonic acid and a salt of said acids.

* * * * *